(12) United States Patent
Rastogi et al.

(10) Patent No.: US 11,857,350 B2
(45) Date of Patent: Jan. 2, 2024

(54) ANALYTE CONCENTRATION ALERT FUNCTION FOR ANALYTE SENSOR SYSTEM

(71) Applicant: Senseonics, Incorporated, Germantown, MD (US)

(72) Inventors: Ravi Rastogi, Columbia, MD (US); Andrew DeHennis, Germantown, MD (US)

(73) Assignee: Senseonics, Incorporated, Germantown, MD (US)

(*) Notice: Subject to any disclaimer, the term of this patent is extended or adjusted under 35 U.S.C. 154(b) by 895 days.

(21) Appl. No.: 16/791,713

(22) Filed: Feb. 14, 2020

(65) Prior Publication Data
US 2020/0178908 A1    Jun. 11, 2020

Related U.S. Application Data

(60) Continuation of application No. 15/485,410, filed on Apr. 12, 2017, now Pat. No. 10,575,793, which is a
(Continued)

(51) Int. Cl.
*A61B 5/1455* (2006.01)
*A61B 5/00* (2006.01)
(Continued)

(52) U.S. Cl.
CPC ............ *A61B 5/746* (2013.01); *A61B 5/0002* (2013.01); *A61B 5/0004* (2013.01); *A61B 5/01* (2013.01);
(Continued)

(58) Field of Classification Search
CPC ..... A61B 5/1455; A61B 5/746; A61B 5/0002; A61B 5/0004; A61B 5/01; A61B 5/1118; A61B 5/14532
See application file for complete search history.

(56) References Cited

U.S. PATENT DOCUMENTS 6,422,066 B1    7/2002  Cordonnier et al.
6,790,178 B1 *  9/2004  Mault .................. G06F 1/1632
                                                                   128/920
(Continued)

FOREIGN PATENT DOCUMENTS

JP    2008-206575 A    9/2008
JP    2010-500078 A    1/2010
(Continued)

*Primary Examiner* — Marjan Fardanesh
(74) *Attorney, Agent, or Firm* — Rothwell, Figg, Ernst & Manbeck, P.C.

(57) ABSTRACT

Systems, methods, and apparatuses that provide alerts based on analyte data and acceleration data. An analyte sensor may generate the analyte data. An accelerometer may generate the acceleration data. A transceiver may convert the analyte data into analyte concentration values. The transceiver may convert the acceleration data into activity information. The transceiver may generate an alert based on the analyte concentration values and activity information. The alert may be communicated to a user by a mobile medical application executed on the transceiver and/or a display device (e.g., smartphone) in communication with the transceiver. The mobile medical application may display (e.g., on a display of the display device) a plot or graph of the analyte concentration values and activity information with respect to time.

21 Claims, 7 Drawing Sheets

Related U.S. Application Data division of application No. 14/559,238, filed on Dec. 3, 2014, now Pat. No. 10,327,714, which is a continuation-in-part of application No. 14/453,078, filed on Aug. 6, 2014, now Pat. No. 10,111,588, which is a continuation-in-part of application No. 13/937,871, filed on Jul. 9, 2013, now Pat. No. 9,414,775, and a continuation-in-part of application No. 13/853,095, filed on Mar. 29, 2013, now Pat. No. 9,345,426.

(60) Provisional application No. 61/922,387, filed on Dec. 31, 2013, provisional application No. 61/912,103, filed on Dec. 5, 2013, provisional application No. 61/881,679, filed on Sep. 24, 2013, provisional application No. 61/865,373, filed on Aug. 13, 2013, provisional application No. 61/864,174, filed on Aug. 9, 2013, provisional application No. 61/617,414, filed on Mar. 29, 2012.

(51) Int. Cl.

| | | |
|---|---|---|
| *A61B 5/11* | (2006.01) | |
| *A61B 5/145* | (2006.01) | |
| *A61B 5/01* | (2006.01) | |
| *A61B 5/1459* | (2006.01) | |
| *A61B 5/0533* | (2021.01) | |

(52) U.S. Cl.
CPC ........... *A61B 5/1112* (2013.01); *A61B 5/1118* (2013.01); *A61B 5/145* (2013.01); *A61B 5/1459* (2013.01); *A61B 5/14532* (2013.01); *A61B 5/7282* (2013.01); *A61B 5/742* (2013.01); *A61B 5/7405* (2013.01); *A61B 5/7455* (2013.01); *A61B 5/0533* (2013.01); *A61B 5/14503* (2013.01); *A61B 5/6898* (2013.01); *A61B 5/7203* (2013.01); *A61B 2562/0219* (2013.01)

(56) References Cited

U.S. PATENT DOCUMENTS

| | | |
|---|---|---|
| 2002/0019586 A1 | 2/2002 | Teller et al. |
| 2002/0128546 A1 | 9/2002 | Silver |
| 2003/0208113 A1* | 11/2003 | Mault ............... G16H 40/63 600/316 |
| 2004/0186390 A1 | 9/2004 | Ross et al. |
| 2005/0236580 A1 | 10/2005 | Colvin et al. |
| 2007/0014726 A1 | 1/2007 | Merical et al. |
| 2007/0163880 A1 | 7/2007 | Woo et al. |
| 2008/0108885 A1 | 5/2008 | Colvin |
| 2008/0208480 A1 | 8/2008 | Kuriyama et al. |
| 2009/0240120 A1 | 9/2009 | Mensinger et al. |
| 2009/0312621 A1 | 12/2009 | Verbitskiy et al. |
| 2010/0024526 A1 | 2/2010 | Colvin, Jr. |
| 2011/0050428 A1 | 3/2011 | Istoc |
| 2011/0193704 A1 | 8/2011 | Harper et al. |
| 2011/0320130 A1 | 12/2011 | Valdes et al. |
| 2012/0029327 A1 | 2/2012 | Angelides |
| 2012/0053427 A1 | 3/2012 | Markle et al. |
| 2012/0130203 A1 | 5/2012 | Stergiou et al. |
| 2012/0223251 A1 | 9/2012 | Morrow et al. |
| 2012/0245444 A1 | 9/2012 | Otis et al. |
| 2013/0120147 A1 | 5/2013 | Narasimhan et al. |
| 2013/0211213 A1 | 8/2013 | DeHennis et al. |
| 2013/0241745 A1 | 9/2013 | Colvin, Jr. et al. |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0018644 A1 | 1/2014 | Colvin, Jr. et al. |
| 2014/0350359 A1 | 11/2014 | Tankiewicz et al. |
| 2015/0141770 A1 | 5/2015 | Rastogi et al. |

FOREIGN PATENT DOCUMENTS

| | | |
|---|---|---|
| WO | 2010/022387 A1 | 2/2010 |
| WO | 2010/141888 A1 | 12/2010 |
| WO | 2011/003035 A2 | 1/2011 |
| WO | 2011/091336 A1 | 7/2011 |
| WO | 2012/123765 A1 | 9/2012 |
| WO | 2013/086564 A1 | 6/2013 |
| WO | 2013/090731 A1 | 6/2013 |
| WO | 2013/149129 A1 | 10/2013 |
| WO | 2015/103022 A1 | 7/2015 |

* cited by examiner

ANALYTE CONCENTRATION ALERT FUNCTION FOR ANALYTE SENSOR SYSTEM

CROSS-REFERENCE TO RELATED APPLICATIONS

The present application is a continuation of U.S. patent application Ser. No. 15/485,410, filed on Apr. 12, 2017, which is a divisional of U.S. patent application Ser. No. 14/559,238, filed on Dec. 3, 2014, now U.S. Pat. No. 10,327,714, all of which are incorporated by reference in their entireties. U.S. patent application Ser. No. 14/559,238 claims the benefit of priority to (1) U.S. Provisional Application Ser. No. 61/912,103, filed on Dec. 5, 2013, and (2) U.S. Provisional Application Ser. No. 61/922,387, filed on Dec. 31, 2013, all of which are incorporated by reference in their entireties. U.S. patent application Ser. No. 14/559,238 is a continuation-in-part of U.S. patent application Ser. No. 14/453,078, filed on Aug. 6, 2014, now U.S. Pat. No. 10,111,588, which claims the benefit of priority to (1) U.S. Provisional Application Ser. No. 61/864,174, filed on Aug. 9, 2013, (2) U.S. Provisional Application Ser. No. 61/865,373, filed on Aug. 13, 2013, and (3) U.S. Provisional Application Ser. No. 61/881,679, filed on Sep. 24, 2013, all of which are incorporated by reference in their entireties. U.S. patent application Ser. No. 14/453,078 is (1) a continuation-in-part of U.S. patent application Ser. No. 13/937,871, filed on Jul. 9, 2013, now U.S. Pat. No. 9,414,775, and (2) a continuation-in-part of U.S. patent application Ser. No. 13/853,095, filed on Mar. 29, 2013, now U.S. Pat. No. 9,345,426, which claims the benefit of priority to U.S. Provisional Application Ser. No. 61/617,414, filed on Mar. 29, 2012, all of which are incorporated by reference in their entireties.

BACKGROUND

Field of Invention

The present invention relates generally to an analyte concentration alert function for an analyte sensor system. Specifically, the present invention relates to a hypoglycemia alert function for a glucose sensor system that generates an alert based on acceleration data.

Discussion of the Background

Diabetes is a metabolic disease in which the body's inability to produce any or enough insulin causes elevated levels of glucose in the blood. Treatment for diabetes includes oral medications and injection or infusion of basal and/or bolus insulin. People with diabetes have an increased risk of hypoglycemia.

Hypoglycemia is defined as a condition characterized by abnormally low blood glucose levels, usually less than 70 mg/dL. Hypoglycemia can also include conditions when the blood glucose of any individual abruptly keeps dropping and goes below a certain threshold (e.g., 70 mg/dL). The most common reasons leading to hypoglycemia in patients include injecting a dose of insulin (e.g., a meal bolus) and then skipping a meal, overdosing on insulin (e.g., through too many injections or through an insulin pump), or strenuous activity (e.g., running or exercising). There are a number of symptoms associated with hypoglycemia (e.g., seizures, etc.). However, a number of people with diabetes either do not exhibit symptoms or are otherwise unaware of their hypoglycemia, a condition known as hypoglycemia unawareness. If left untreated, hypoglycemia has the potential to lead to fatal situations, such as accidents, injuries, unconsciousness, seizures, coma, and, in some cases, death.

Typically, hypoglycemia is treated with the consumption of carbohydrates to restore blood glucose to safe levels and prevent the progression to severe hypoglycemia. People with diabetes need to maintain a log of the amount of daily carbohydrates consumed in order to adequately treat their diabetes. Errors in carbohydrate counting can lead to miscalculated doses of insulin which in turn can lead to hypoglycemia. In severe cases of hypoglycemia (e.g. during seizures and/or unconsciousness) an emergency injection of the hormone glucagon may be required (i.e. a glucagon rescue) to raise the blood glucose to a safe level.

Although some continuous glucose monitors (CGMs) alert users when negative glucose trends are detected and alarm users when the blood glucose falls below a user-defined threshold, these alerts are provided to users when the patient is already hypoglycemic or about just about to be hypoglycemic.

There is presently a need in the art for a continuous analyte monitor with an improved hypoglycemic alert function.

SUMMARY

One aspect of the invention may provide a method of alerting for a current or projected physiological condition or reaction. In some embodiments, the method may comprise generating acceleration data corresponding to movement of an accelerometer, generating activity information based on the acceleration data, and generating an alert for the current or projected physiological condition or reaction based on the activity information. In some embodiments, the method may further comprise displaying the alert. The display of the alert may be by a mobile medical application executed by a processor of, for example, a display device. In some embodiments, the display device may be, for example, a smartphone. In some embodiments, the accelerometer may be located, for example, within a transceiver, an analyte sensor and/or an activity tracker. In some embodiments, the physiological condition or reaction may be, for example, hypoglycemia, dehydration and or hyperglycemia. In some embodiments, the alert may be a predictive alert.

In other embodiments, the method may further comprise receiving galvanic or physiologic measurements from an on-body or within body sensor, wherein the activity information is generated based on the acceleration data and the galvanic or physiologic measurements. In embodiments wherein the accelerometer is located in a transceiver, the method may further comprise receiving activity information from an activity tracker, and wherein the alert is additionally based on the activity information received from the activity tracker. In some embodiments, the method may comprise generating analyte concentration values based on data signals received from an analyte sensor, wherein generating the alert comprises generating the alert based on the activity information and the analyte concentration values.

In some embodiments, the method may comprise displaying a plot of the analyte concentration values and the activity information with respect to time. In some embodiments, the plot may be generated by a mobile medical application executed by a processor of a display device, and the plot may be displayed on a display of the display device. In some embodiments, the method may comprise using a transceiver to receive the data signals from the analyte sensor, and using the transceiver to generate the analyte concentration values. In some embodiments, the method may comprise using the transceiver to convey the data signals to a display device, and using a mobile medical application executed by a processor of the display device to generate the analyte concentration values.

In some embodiments, generating activity information based on the acceleration information may comprise converting the acceleration data into scalar acceleration values, comparing the scalar acceleration values to an activity threshold, and generating activity information based on the frequency of acceleration values that exceed the activity threshold. In some embodiments, the activity information may be used to detect sleep patterns and/or to detect step counts. In some embodiments, generating activity information based on the acceleration information may comprise converting the acceleration data into scalar acceleration values, comparing the scalar acceleration values to an activity threshold, and generating activity information based on the frequency of acceleration values that exceed the activity threshold. In some embodiments, a transceiver may be used to generate the activity information.

In some embodiments, a mobile medical application executed by a processor of a display device may be used to generate the activity information and/or generate the alert. In some embodiments, a transceiver may be used to receive the generated activity information and/or to generate the alert.

In another aspect of the invention, a system may be provided which comprises an accelerometer configured to generate acceleration data corresponding to movement of the accelerometer, and a transceiver configured to generate or receive activity information based on the acceleration data and to generate an alert for a current or projected physiological condition or reaction based on the activity information. In some embodiments, the transceiver may comprise the accelerometer. Some embodiments may comprise an analyte sensor where in the analyte sensor comprises the accelerometer. In some embodiments, the transceiver is configured to receive data signals from the analyte sensor, generate analyte concentration values based on the received data signals, and generate the alert based on the analyte concentration values, and the activity information.

In some embodiments, the system comprises a display configured to display the analyte concentration values and the activity information with respect to time. In some embodiments, the display is configured to display a plot or graph of the analyte concentration values and the activity information with respect to time. In some embodiments, the display device may include a transceiver interface device configured to receive the alert, the analyte concentration values, and the activity information from the transceiver; a processor configured to execute a mobile medical application configured to generate a display of the alert, the analyte concentration values, and the activity information; and a display configured to display the generated display.

In some embodiments, to generate the activity information based on the acceleration data, the transceiver may be configured to convert the acceleration data into scalar acceleration values, compare the scalar acceleration values to an activity threshold, and generate activity information based on the frequency of acceleration values that exceed the activity threshold. In some embodiments, the system may comprise an activity tracker, wherein the activity tracker comprises the accelerometer. In some embodiments, the transceiver may comprise the accelerometer and may be further configured to receive activity information from the activity tracker, and generate the alert based on (i) the activity information generated by the transceiver and (ii) the activity information received from the activity tracker. In some embodiments, the transceiver may be further configured to receive galvanic or physiologic measurements from an on-body or within body sensor, and generate the activity information based on the acceleration data and the galvanic or physiologic measurements.

In another aspect of the invention, an apparatus may be provided which comprises a sensor interface device configured to receive data signals from an analyte sensor; an accelerometer configured to generate acceleration data corresponding to movement of the accelerometer; and circuitry configured to generate analyte concentration values based on the received data signals, generate activity information based on the acceleration data, and generate an alert based on the analyte concentration values and the activity information. In some embodiments, the apparatus may comprise an interface device configured to receive analyte concentration values and activity information, circuitry configured to generate a plot of the analyte concentration values and the activity information with respect to time, and a display configured to display the plot.

In another aspect of the invention, a method may be provided for alerting for a current or projected physiological condition or reaction based on informatics generated by accelerometer measurements.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
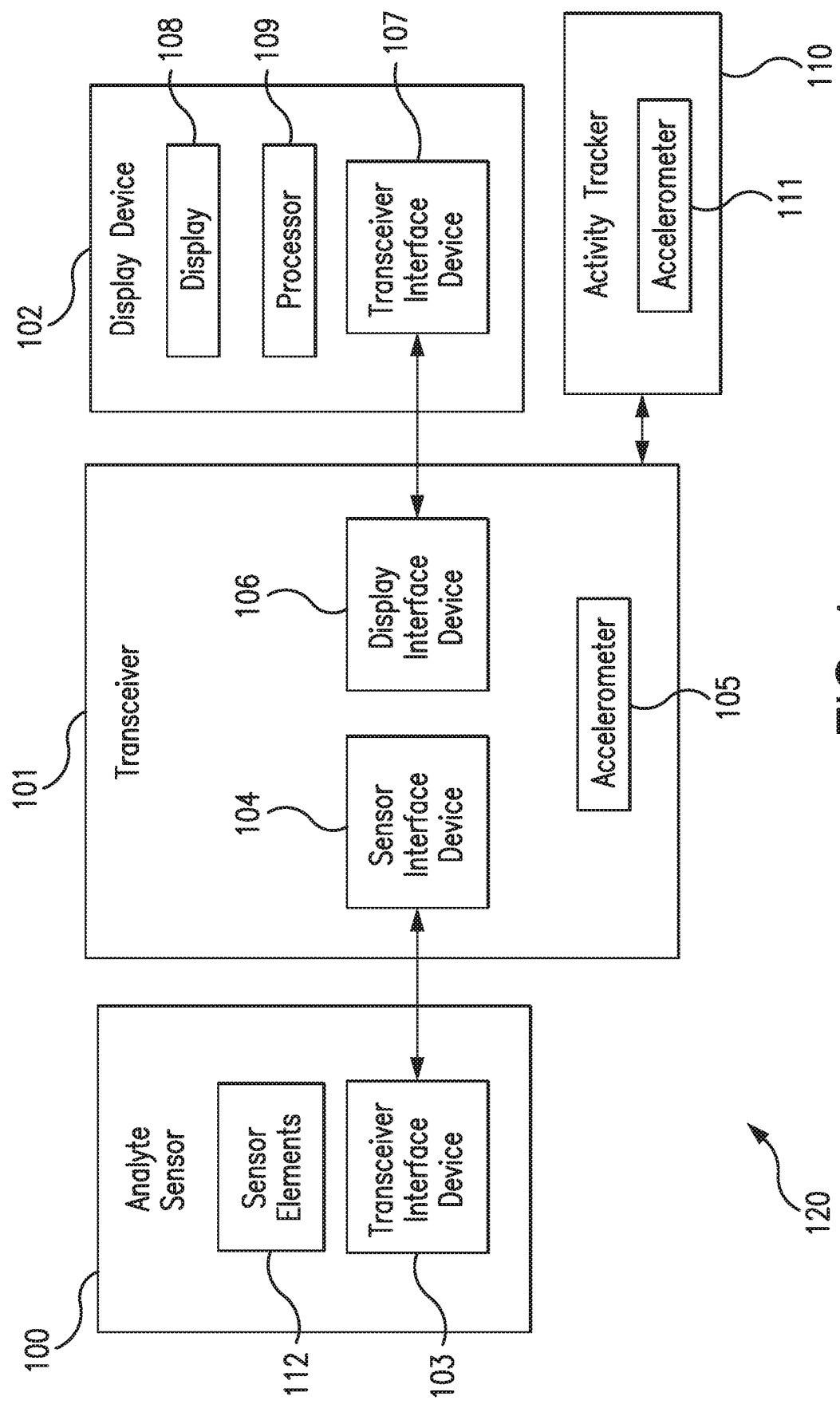
FIG. 1 is a schematic view illustrating an analyte monitoring system embodying aspects of the present invention.

FIG. 1 is a schematic view of a continuous analyte monitoring system 120 embodying aspects of the present invention. In some embodiments, the system 120 may include one or more of an analyte sensor 100, a transceiver 101, a display device 102, and an activity tracker 110. In some embodiments, the sensor 100 and transceiver 101 may include one or more of the structural and/or functional features described in one or more of U.S. Patent Application Publication No. 2013/0241745; U.S. Patent Application Publication No. 2013/0211213; U.S. application Ser. No. 14/453,078; and U.S. Patent Application Publication No. 2014/0018644; all of which are incorporated by reference in their entireties.

In some embodiments, system 120 may include one or more accelerometers (e.g., accelerometer 105 and/or accelerometer 111), which may be, for example, 3D accelerometers. In some embodiments, the one or more accelerometers may be configured to generate acceleration data corresponding to movement of the accelerometer. In some embodiments, the continuous analyte monitoring system 120 may use the one or more accelerometers to keep track of near continuous movements of a user's upper arm, wrist, leg, or core, for example. In some embodiments, the one or more accelerometers may be located in or part of one or more of the analyte sensor 100, transceiver 101, display device 102, and activity tracker 110. In some non-limiting embodiments, as illustrated in FIG. 1, the transceiver 101 may include an accelerometer 105. In some non-limiting embodiments, as illustrated in FIG. 1, the system 120 may include an activity tracker 110 (e.g., an on-body activity tracker such as, for example and without limitation, a fitbit), which may include an accelerometer 111 in addition to or as an alternative to the accelerometer 105. In some non-limiting embodiments, the analyte sensor 100 and/or display device 102 may additionally or alternatively include an accelerometer. In some embodiments, the transceiver 101 may be configured to generate activity information based on acceleration data generated by one or more accelerometers and may be configured to generate one or more alerts based on the activity information. In some embodiments, the transceiver 101 may be configured to additionally or alternatively receive activity information (e.g., from display device 102 or activity tracker 110) that was generated (e.g., by display device 102 or activity tracker 110) based on acceleration data generated by one or more accelerometers. In some embodiments, the transceiver 101 and/or display device 102 may communicate the one or more alerts to a user. In some embodiments, the alerts may be visual, audible, and/or vibratory alerts.

In some embodiments, the transceiver 101 may be configured to receive data signals from the analyte sensor 100 and may be configured to generate analyte concentration values based on the received data signals. In some embodiments, the transceiver 101 may be configured to generate one or more alerts based on the analyte concentration values and the activity information. In some embodiments, the system 120 may include one or more displays. For example, in one non-limiting embodiment, the system 120 may include a display device 102, and the display device 102 may include a display 108 configured to display (e.g., in a plot or graph) one or more of the analyte concentration values and the activity information with respect to time. In some embodiments, the transceiver 101 may additionally or alternatively include a display configured to display one or more of the analyte concentration values and the activity information with respect to time.

In some embodiments, the analyte sensor 100 may include sensor elements 112 and a transceiver interface device 103. The sensor elements 112 may be configured to detect the presence and/or concentration of an analyte (e.g., glucose, oxygen, cardiac markers, low-density lipoprotein (LDL), high-density lipoprotein (HDL), or triglycerides). In some non-limiting embodiments, the sensor elements 112 may include one or more of an analyte indicator, a light source configured to emit excitation light to the analyte indicator, and a photodetector configured to receive light from the analyte indicator. The amount of light received by the photodetector may be indicative of the presence or concentration of the analyte. Although, in some embodiments, as described above, the analyte sensor 100 may be an electro-optical sensor, this is not required, and, in some alternative embodiments, the analyte sensor 100 may be another type of analyte sensor, such as, for example and without limitation, an electro-chemical sensor.

In some embodiments, the transceiver interface device 103 may be configured to (i) receive a power signal and generate power for powering the sensor elements 112 and/or (ii) convey data signals generated by the sensor elements 112. In some non-limiting embodiments, the transceiver interface device 103 may be configured to wirelessly convey data signals, and the transceiver interface device 103 may include an inductive element (e.g., an antenna or coil). In some alternative embodiments, the transceiver interface device 103 may be configured to convey data signals via a wired connection to an external device (e.g., transceiver 101), and the transceiver interface device 103 may include the wired connection.

In some non-limiting embodiments, the analyte sensor 100 may be an implantable sensor or a transcutaneous sensor. In some embodiments, the sensor 100 may be implanted or inserted in a living animal (e.g., a living human). The sensor 100 may be implanted or inserted, for example, in a living animal's arm, wrist, leg, abdomen, peritoneum, intravenously, or other region of the living animal suitable for sensor implantation or insertion. For example, in one non-limiting embodiment, the sensor 100 may be implanted beneath the skin (i.e., in the subcutaneous or peritoneal tissues) such that no portion of the sensor 100 protrudes from the skin, and the transceiver interface device 103 may convey data signals wirelessly. Although, in some embodiments, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating (e.g., using inductive elements), the sensor 100 and transceiver 101 may communicate using one or more wires connected between the transceiver 101 and the transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the transceiver 101 may be an electronic device that communicates with the sensor 100 to power the sensor 100 and/or receive data signals (e.g., photodetector and/or temperature sensor readings) from the analyte sensor 100. In some embodiments, the transceiver 101 may include a sensor interface device 104. The sensor interface device 104 of the transceiver 101 may be configured to receive the data signals from the analyte sensor 100 using wireless (e.g., inductive) and/or wired communication. In some embodiments where data signals are wirelessly conveyed between the transceiver 101 and the analyte sensor 100, the communication between the transceiver 101 and the analyte sensor 100 may be, for example and without limitation, near field communication.

In some embodiments (e.g., embodiments in which the sensor 100 is a fully implantable sensor), the transceiver 101 may implement a passive telemetry for communicating with the implantable sensor 100 via an inductive magnetic link for one or more of power and data transfer. In some embodiments, the magnetic transceiver-sensor link can be considered as "weakly coupled transformer" type. The magnetic transceiver-sensor link may provide energy and a link for data transfer using amplitude modulation (AM). Although in some embodiments, data transfer is carried out using AM, in alternative embodiments, other types of modulation may be used. In some non-limiting embodiments, the analyte monitoring system may use a frequency of 13.56 MHz, which can achieve high penetration through the skin and is a medically approved frequency band, for power and/or data transfer. However, this is not required, and, in other embodiments, one or more different frequencies may be used for powering and communicating with the sensor 100.

In some non-limiting embodiments, the transceiver 101 may be a handheld transceiver or a body-worn transceiver (e.g., a transceiver held in place by a wristwatch, an armband, belt, or adhesive). For example, in some embodiments where the transceiver 101 is an on-body/wearable device, the transceiver 101 may be held in place by a band (e.g., an armband or wristband) and/or adhesive (e.g., as part of a biocompatible patch), and the transceiver 101 may convey (e.g., periodically, such as every two minutes, and/or upon user initiation) measurement commands (i.e., requests for measurement information) to the sensor 100. In some embodiments where the transceiver 101 is a handheld device, positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive a reading from the sensor 100.

In some embodiments, the transceiver 101 may calculate analyte concentrations from the analyte data received from the sensor 100. However, it is not required that the transceiver 101 perform the analyte concentration calculations itself, and, in some alternative embodiments, the transceiver 101 may instead convey/relay the analyte data received from the sensor 100 to another device (e.g., display device 105) for calculation of analyte concentrations (e.g., by a mobile medical application executing on the display device 105). In some non-limiting embodiments, the analyte concentration calculation may include one or more features described in U.S. Patent Application Publication No. 2014/0018644, which is incorporated by reference in its entirety.

In some embodiments, the transceiver 101 may include a display interface device 106 configured to convey information (e.g., alerts and/or analyte concentrations) to one or more display devices 102. In some embodiments, a display device 102 may be a portable and/or handheld device. In some embodiments, the display device 105 may be a smartphone. However, this is not required, and, in alternative embodiments, the display device 102 may be a laptop computer, tablet, notebook, personal data assistant ("PDA"), personal computer, or a dedicated analyte monitoring display device. In some embodiments, the display device 102 may include a transceiver interface device 107, which may be configured to communicate with the display interface device 106 of the transceiver 101 through a wired or wireless connection. In some embodiments, the display device 102 may include a processor 109, and the display device 102 may have a mobile medical application installed thereon. In some non-limiting embodiments, the processor 109 may execute the mobile medical application.

Figure 2:
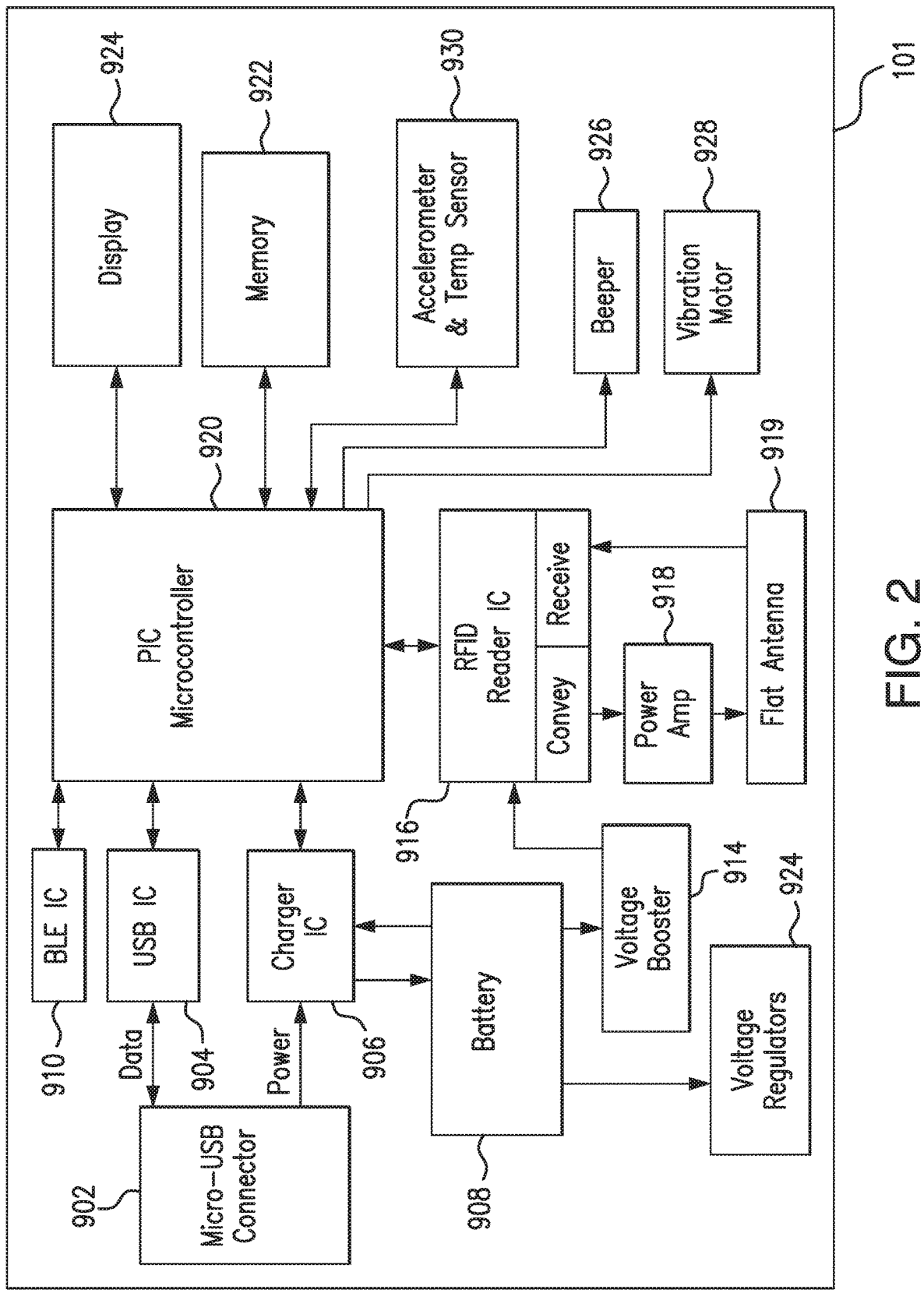
FIG. 2 is a schematic view illustrating a transceiver embodying aspects of the present invention.

FIG. 2 is a schematic view of a transceiver 101 according to a non-limiting embodiment. In some embodiments, the display interface device 106 of the transceiver 101 may include an antenna of a wireless communication integrated circuit (IC) 910 and/or a connector 902. In some non-limiting embodiments, the display interface device 106 may additionally include the wireless communication IC 910 and/or a connector IC 904.

In some embodiments, the connector 902 may be, for example, a Micro-Universal Serial Bus (USB) connector. The connector 902 may enable a wired connection to an external device, such as a display device 102 (e.g., a smartphone or a personal computer). The transceiver 101 may exchange data to and from the external device through the connector 902 and/or may receive power through the connector 902. The connector IC 904 may be, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a display device 105 (e.g., a smartphone or a personal computer) and/or to receive power, which may be used, for example, to charge the battery 908.

In some embodiments, the wireless communication IC 910 may enable wireless communication with an external device, such as, for example, one or more display devices 105 (e.g., a smartphone or personal computer). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna).

In some embodiments, the transceiver 101 may include voltage regulators 912 and/or a voltage booster 914. The battery 908 may supply power (via voltage booster 914) to radio-frequency identification (RFID) reader IC 916, which uses an inductive element 919 to convey information (e.g., commands) to the sensor 100 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 919 is a flat antenna. In some non-limiting embodiments, the antenna may be flexible. However, the inductive element 919 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 919 to the sensor 100.

The transceiver 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transceiver 101. For example, the PIC microcontroller 920 may control the connector IC 904 or wireless communication IC 910 to transmit data via wired or wireless communication and/or control the RFID reader IC 916 to convey data via the inductive element 919. The PIC microcontroller 920 may also control processing of data received via the inductive element 919, connector 902, or wireless communication IC 910.

In some embodiments, the transceiver 101 may include a sensor interface device, which may enable communication by the transceiver 101 with a sensor 100. In some embodiments, the sensor interface device may include the inductive element 919. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which PIC microcontroller 920 may control to display data (e.g., glucose concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer (e.g., accelerometer 105) and/or temperature sensor, that may be used in the processing performed by the PIC microcontroller 920.

In some embodiments, the transceiver 101 may be a body-worn transceiver that is a rechargeable, external device worn over the sensor implantation or insertion site. The transceiver 101 may supply power to the proximate sensor 100, calculate analyte concentrations from data received from the sensor 100, and/or transmit the calculated analyte concentrations to a display device 105 (see FIGS. 1A, 1B, and 5). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2 minutes) read sensor data and calculate an analyte concentration and an analyte concentration trend. From this information, the transceiver 101 may also determine if an alert and/or alarm condition exists, which may be signaled to the user (e.g., through vibration by vibration motor 928 and/or an LED of the transceiver's display 924 and/or a display of a display device 105). The information from the transceiver 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application on the display device 105. In some non-limiting embodiments, the mobile medical application may provide alarms, alerts, and/or notifications in addition to any alerts, alarms, and/or notifications received from the transceiver 101. In one embodiment, the mobile medical application may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 may provide on-body alerts to the user in a visual, audible, and/or vibratory manner, regardless of proximity to a display device 105. In some non-limiting embodiments, as illustrated in FIG. 2, the transceiver 101 may include one or more notification devices (e.g., display 924, beeper 926, and/or vibration motor 928) that generate visual, audible, and/or vibratory alerts. In some embodiments, the transceiver 100 may be configured to vibrate and/or generate an audio or visual signal to prompt the user about analyte readings outside an acceptable limit, such as hypo/hyper glycemic alerts and alarms in the case where the analyte is glucose.

In some embodiments, the transceiver 101 may store the measurement information received from the sensor 100 (e.g., in memory 922). The measurement information received from the sensor 100 may include one or more of: (i) a signal channel measurement with a light source on, (ii) a reference or second signal channel measurement with the light source on, (iii) a light source current source voltage measurement, (iv) a field current measurement, (v) a diagnostic measurement, (vi) an ambient signal channel measurement with the light source off, (vii) an ambient reference or second signal channel measurement with the light source off, and (viii) a temperature measurement. In some embodiments, the transceiver 101 may additionally store (e.g., in memory 922) other data with the measurement information received from the sensor 100. In some non-limiting embodiments, the other data may include one or more of: (i) an analyte concentration (e.g., in mg/dL, such as, for example, within a range of 20.0 to 400.0 mg/dL) calculated by the transceiver 101 from the measurement information, (ii) the date and time that the analyte measurement was taken, (iii) accelerometer values (e.g., x, y, and z) taken from an accelerometer (e.g., accelerometer 105 of the transceiver 101 and/or accelerometer 111 of the activity tracker 110), and/or (iv) the temperature of the transceiver 101 as measured by a temperature sensor of the transceiver 101. In some embodiments, the transceiver 101 may keep track of the date and time and, as noted above, store the date and time along with the received analyte measurement information and/or analyte concentrations.

In embodiments where the transceiver 101 includes an accelerometer, the accelerometer will enable tracking of activity levels of the subject that is wearing the transceiver 101. This activity level may be included in an event log and incorporated into various algorithms (e.g., for analyte concentration calculation, trending, and/or contributing to potential dosing levels for the subjects). In some embodiments, the transceiver 101 may store (e.g., in memory 922) any alert and/or alarm conditions detected based on the calculated analyte concentrations.

In some embodiments, the continuous analyte monitoring system 120 may keep track of an analyte concentration (e.g., blood glucose concentration) in the user. In some embodiments, the continuous analyte monitoring system may facilitate user entry of one or more measurable physiological parameters (e.g., insulin and/or meal bolus and/or exercise regimen) on a mobile medical application. The mobile medical application may be running/executed on (a) the transceiver 101 and/or (b) the display device 102 (e.g., smartphone, receiver, laptop, tablet, notebook, or personal computer) in communication with the transceiver 101, analyte sensor 100, and/or activity tracker 110. For example, in one non-limiting embodiment, the mobile medical application may be executed by a processor 109 of the display device 102. In some embodiments having a smartphone or other display device 102 in communication with the transceiver, the communication between the transceiver 101 and the smartphone or other display device 102 may be wireless communication (e.g., using the Bluetooth wireless communication standard) or wired communication, and the smartphone or other display device 102 may receive information (e.g., analyte concentrations) from the transceiver 101.

In some embodiments, the continuous analyte monitoring system 120 may combine analyte concentration information with measurable physiological parameters to provide alerts regarding a current or projected physiological condition. For example, in some embodiments where the analyte is glucose, the continuous glucose monitoring system 120 may fuse glucose concentration information with measurable physiological parameters to provide alerts regarding a current or projected hypoglycemic condition. In some embodiments, the alerts may include predictive alerts that could be used to prevent a projected physiological condition. For instance, in some non-limiting embodiments, predictive alerts could be used to prevent hypoglycemic episodes (e.g., night time hypoglycemic episodes or in cases of hypoglycemia unawareness) that are preceded by extended duration of activity detected using the accelerometer. For example, the continuous analyte monitoring system may provide alerts to the mobile medical application which would trigger a text alert on the smartphone or other display device 102 such as "No meal was taken following extended activity. Please eat before going to sleep."

Figure 3:
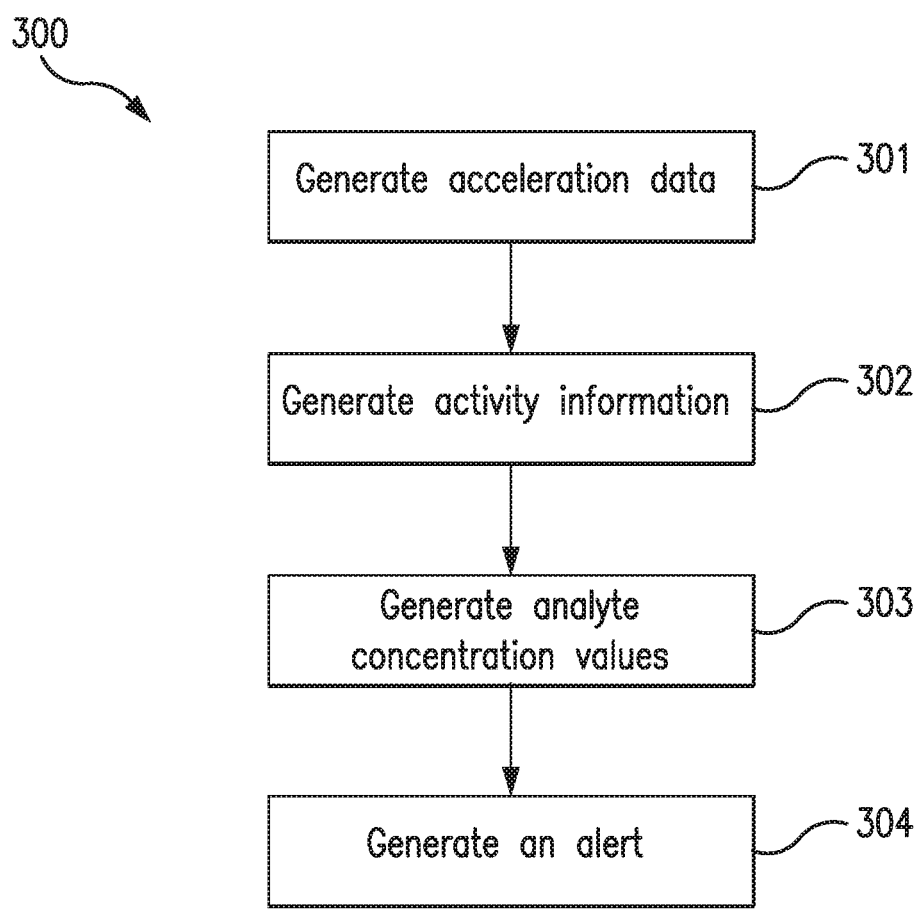
FIG. 3 is a flow chart illustrating an alerting process embodying aspects of the present invention.

FIG. 3 is a flow chart illustrating an alerting process 300 embodying aspects of the present invention. In some embodiments, the alerting process 300 may include a step 301 of generating acceleration data corresponding to movement of an accelerometer. In some embodiments, the acceleration data may be generated by one or more accelerometers (e.g., accelerometer 105 and/or accelerometer 111), which may be located in one or more of the analyte sensor 100, transceiver 101, display device 102, and activity tracker 111.

In some embodiments, the alerting process 300 may include a step 302 of generating activity information based on the acceleration data. In some embodiments, the activity information may be generated by one or more of the transceiver 101 (e.g., by the microcontroller 920 of transceiver 101), the display device 102 (e.g., by a mobile medical application being executed on the processor 109 of the display device 102), and the activity tracker 111.

In some embodiments, the alerting process 300 may include a step 303 of generating analyte concentration values based on data signals received from the analyte sensor 100. In some embodiments, the analyte concentration values may be generated by one or more of the transceiver 101 (e.g., by the microcontroller 920 of transceiver 101) and the display device 102 (e.g., by a mobile medical application being executed on the processor 109 of the display device 102). Although, in the embodiment illustrated in FIG. 3, the step 303 of generating analyte concentration values occurs after steps 301 and 302, this is not required, and, in some alternative embodiments, the step 303 may occur before or during with one or more of steps 301 and 302.

In some embodiments, the alerting process 300 may include a step 304 of generating an alert for the current or projected physiological condition or reaction based on one or more of the activity information and the analyte concentration values. In some embodiments, the alert may be generated by one or more of the transceiver 101 (e.g., by the microcontroller 920 of transceiver 101) and the display device 102 (e.g., by a mobile medical application being executed on the processor 109 of the display device 102).

In some embodiments, an accelerometer (e.g., accelerometer 105) may be placed inside a printed circuit board (PCB) of the transceiver 101, and the accelerometer may be used to detect the movements of the user's body (e.g., the user's upper body in an embodiment where the transceiver is worn on the arm or the user's core when the transceiver is worn on the abdomen). In some embodiments, outputs of the accelerometer may correspond to accelerations along the X, Y and Z axis. In some embodiments, the outputs may be analog values that have been converted to digital values by an analog-to-digital converter (ADC). The accelerometer outputs may be used to interpret and quantify the movements of the user(s) wearing the transceiver.

Figure 4:
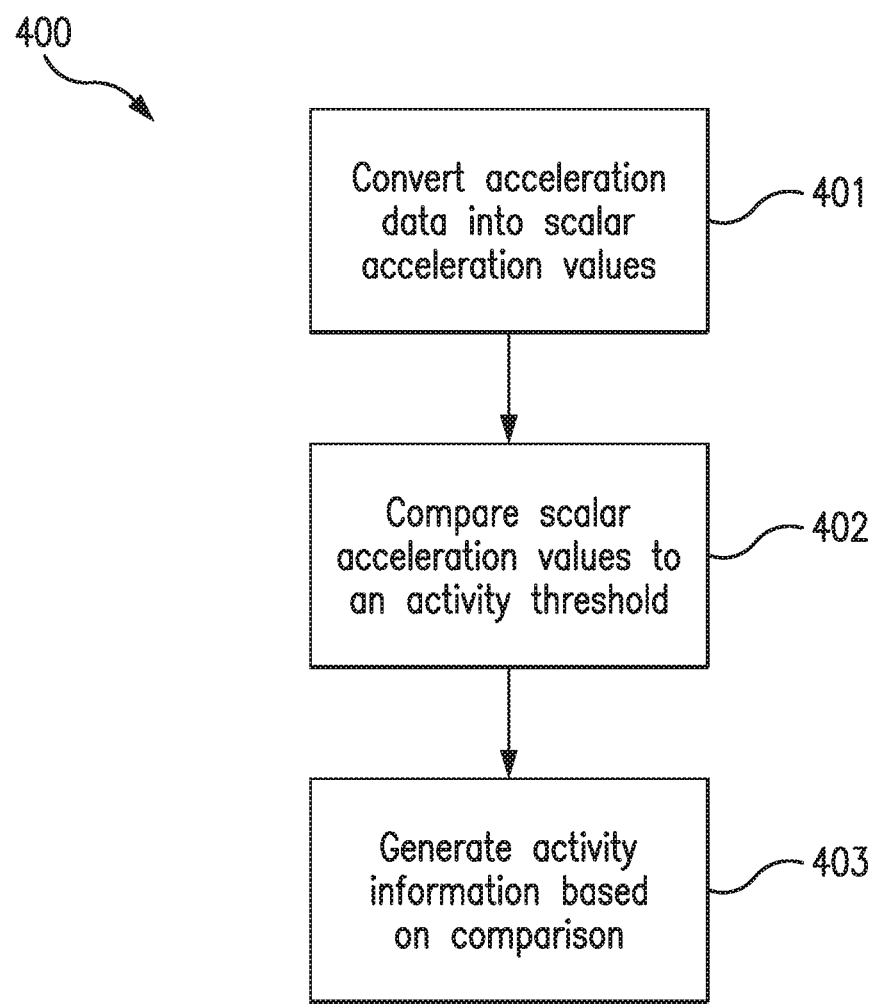
FIG. 4 is a flow chart illustrating an activity information generation process embodying aspects of the present invention.

FIG. 4 is a flow chart illustrating an activity information generation process 400 embodying aspects of the present invention. In some non-limiting embodiments, the process 400 may be performed in step 302 of the alerting process 300. In some embodiments, the activity information generation process 400 may include a step 401 of converting accelerating data into scalar acceleration values. In some embodiments, the conversion of step 401 may include converting raw data (e.g., digital values) from the accelerometer to g's (m/sec2). In some embodiments, the conversion of step 401 may include converting the resultant data to a scalar value. In some non-limiting embodiments, the resultant data may be converted to scalar values using the formula shown below:

$$AccScalar = sqrt(X*X + Y*Y + Z*Z) \quad \text{(Formula 1)}$$

Figure 5:
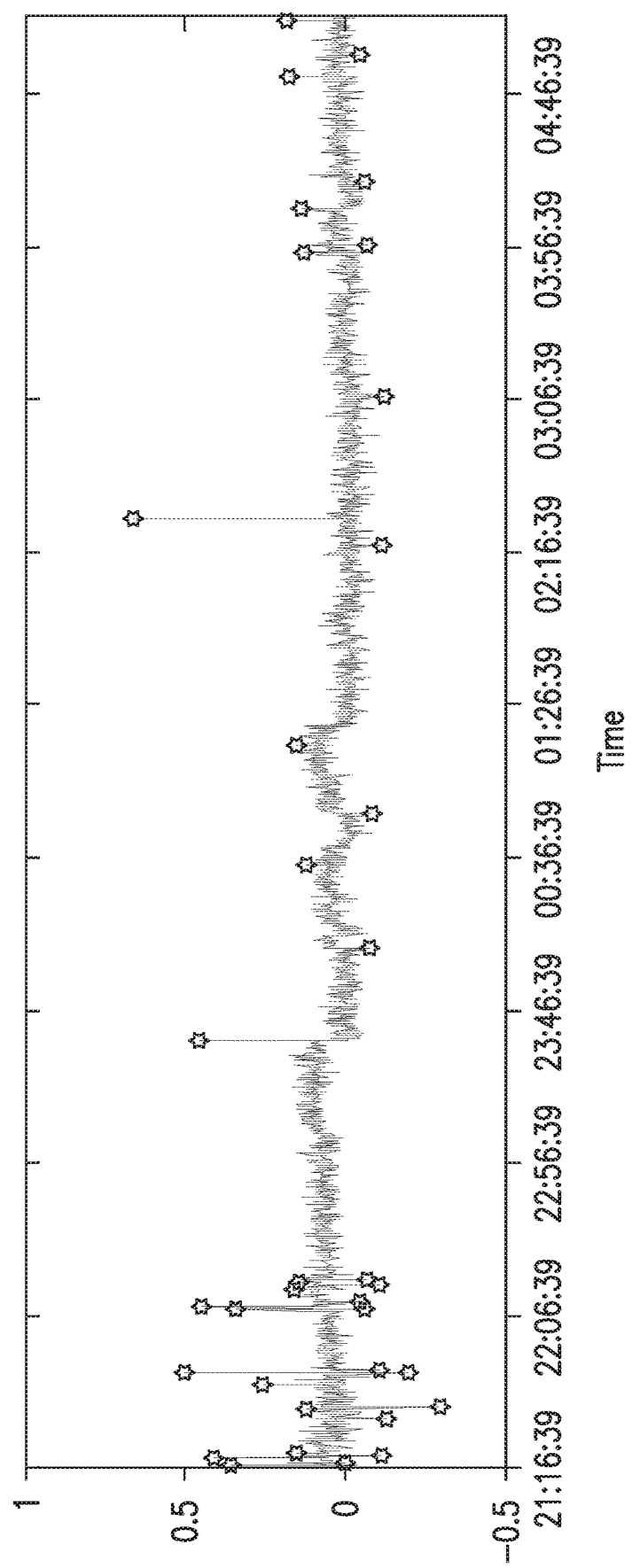
FIG. 5 is a graph showing scalar acceleration values measured by a system embodying aspects of the present invention.

In some embodiments, circuitry (e.g., microcontroller 920) of the transceiver 101 may carry out the conversion of the accelerometer raw data to g's and from the g's to the scalar values. However, this is not required, and in other embodiments a portion or all of the conversions may be carried out elsewhere, such as, for example and without limitation, by the display device 102 (e.g., a smartphone or personal computer) and/or by the activity tracker 110. FIG. 5 is a graph showing a non-limiting example of scalar acceleration values (black line) of an accelerometer over time.

In some embodiments, the process 400 may include a step 403 of comparing scalar acceleration values to one or more activity thresholds. That is, in some embodiments, the continuous analyte monitoring system 120 may use the scalar acceleration values to detect abrupt changes in acceleration based on one or more cutoff thresholds. These instances of high changes in acceleration typically correspond to changes in the position of the body and, thus, activity. Accordingly, in some non-limiting embodiments, the continuous analyte monitoring system 120 may detect activity by detecting when a scalar acceleration value exceeds the cutoff threshold (i.e., an activity threshold). FIG. 5 shows detected activities (stars) based on an activity threshold of 0.18 in the non-limiting example. Although an activity threshold of 0.18 is used in the embodiment shown in FIG. 5, this is not required, and alternative embodiments may use one or more different activity thresholds.

Figure 6:
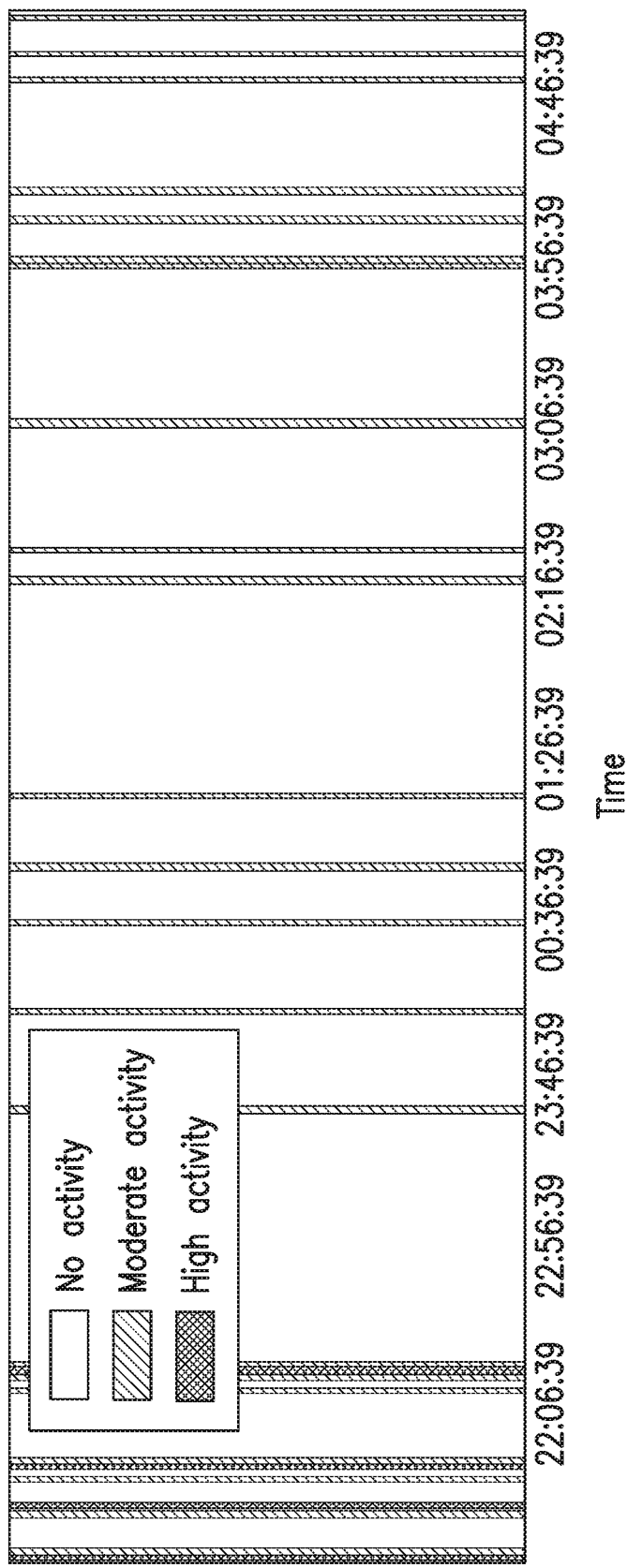
FIG. 6 is a graph showing the intensity and duration of the physical activity of a patient measured by a system embodying aspects of the present invention.

In some embodiments, the process 400 may include a step 403 of generating activity information based on the frequency of acceleration values that exceed the activity threshold. In some non-limiting embodiments, the step 403 may use the frequency of detected activities (e.g., within a time window) to characterize the activity in the acceleration information into three main categories: no activity/sedentary, moderate activity, and high activity. FIG. 6 is a graph showing an exemplary classification of the detected activity in the acceleration information into no activity, moderate activity, and high activity categories. Accordingly, FIG. 6 shows the intensity and duration of the physical activity of the user.

Figure 7:
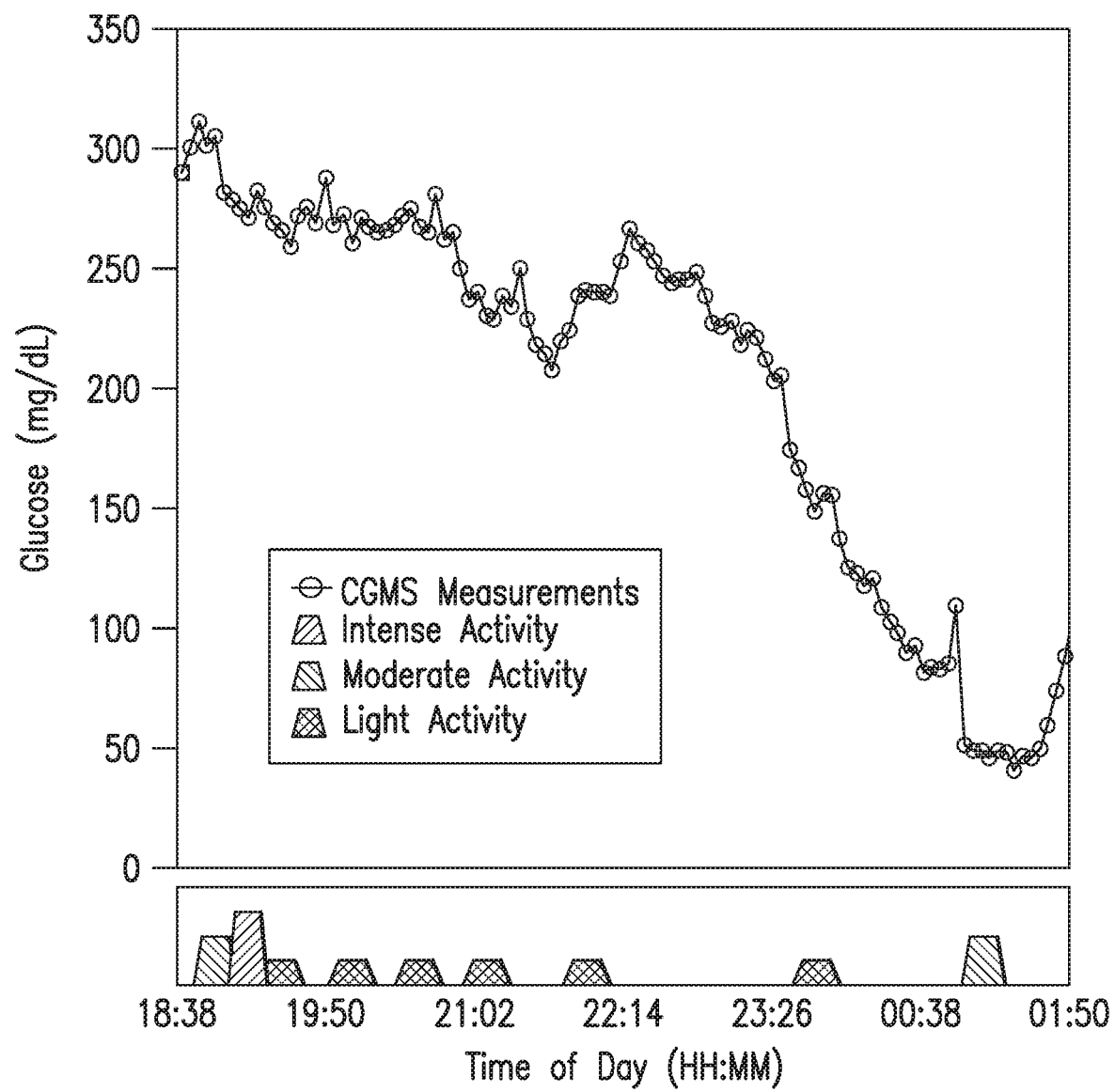
FIG. 7 is a graph showing the glucose and activity measurements measured by a system embodying aspects of the present invention.

In some embodiments, this information about the activity may be (i) provided to the user independently as a graph generated by the mobile medical application and displayed on a display (e.g., display 108 of the display device 102) and/or (ii) fused with the analyte data from continuous analyte monitoring system for providing predictive alerts of possible health condition episodes (e.g., hypoglycemic episodes) before they happen. FIG. 7 is a graph showing an example of analyte measurements (e.g., continuous glucose monitoring system (CGMS) measurements) together with activity monitoring data. The graph may be displayed, for example and without limitation, by the display 108 of the display device 102 and/or by the display 924 of the transceiver 101.

In some embodiments, the continuous analyte monitoring system 120 may additionally or alternatively use the activity information to detect sleep patterns and/or step counts, which may be provided to the user using graphs and/or bar plots. In some non-limiting embodiments, the graphs and/or plots may be, for example and without limitation, generated by a mobile medical application running on processor 109 of the display device 102 and displayed by display 108 of the display device 102.

In some non-limiting embodiments, the continuous analyte monitoring system 120 may use galvanic or physiologic measurements (e.g., heartrate, heartbeat, and/or sweating) generated by one or more on-body or within body sensors in conjunction with the acceleration data generated by the one or more accelerometers to generate the activity information and generate the alerts regarding a current or projected physiological condition or reaction.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A system comprising:
an analyte sensor configured to generate analyte data;
an accelerometer configured to generate acceleration data corresponding to movement of the accelerometer;
a display device; and
a wearable transceiver comprising a memory, a display device interface, and a controller configured to (i) store the analyte data in the memory with the acceleration data and date and time information and (ii) cause the display device interface to convey the analyte data, the acceleration data, and the date and time information to the display device;
wherein the display device is configured to (i) receive the analyte data, the acceleration data, and the date and time information conveyed by the display device interface of the wearable transceiver and (ii) calculate a current analyte concentration value using at least the analyte data and the acceleration data.

2. The system of claim 1, wherein the display device is configured to generate activity information based on the acceleration data, and calculating the current analyte concentration value using at least the analyte data and the acceleration data comprises calculating the current analyte concentration value using at least the analyte data and the activity information generated based on the acceleration data.

3. The system of claim 1, wherein the wearable transceiver comprises the accelerometer.

4. The system of claim 1, wherein the display device interface comprises an antenna.

5. The system of claim 1, wherein the display device interface comprises a wireless communication integrated circuit.

6. The system of claim 1, further comprising an adhesive patch configured to hold the wearable transceiver in place on a body of a patient.

7. A system of claim 2, comprising:
an analyte sensor configured to generate analyte data;
an accelerometer configured to generate acceleration data corresponding to movement of the accelerometer;
a wearable transceiver comprising a memory, a display device interface, and a controller configured to store the analyte data in the memory with the acceleration data and date and time information;
a display device configured to (i) receive the analyte data, the acceleration data, and the date and time information conveyed by the wearable transceiver and (ii) generate activity information based on the acceleration data, wherein generating the activity information based on the acceleration information comprises:
converting the acceleration data into scalar acceleration values;
comparing the scalar acceleration values to an activity threshold; and
generating the activity information based on a frequency at which the scalar acceleration values exceed the activity threshold.

8. The system of claim 7, wherein the display device is configured to calculate an analyte concentration value using at least the analyte data.

9. The system of claim 8, wherein the display device is configured to calculate an analyte concentration value using at least the analyte data and the activity information.

10. The system of claim 8, wherein the display device is configured to display the analyte concentration value together with the activity information.

11. The system of claim 8, wherein the display device is configured to display a plot of analyte concentration values and activity information with respect to time.

12. The system of claim 8, wherein the display device is configured to generate an alert for a current or projected physiological condition or reaction based on the analyte concentration value and the activity information.

13. A method comprising:
using an analyte sensor to generate analyte data;
using an accelerometer to generate acceleration data corresponding to movement of the accelerometer;

using a controller of a wearable transceiver to store the analyte data with the acceleration data and date and time information in a memory of the wearable transceiver;

using the controller of the wearable transceiver to cause a display device interface of the wearable transceiver to convey the analyte data, the acceleration data, and the date and time information to a display device;

using the display device to receive the analyte data, the acceleration data, and the date and time information conveyed by the wearable transceiver; and using the display device to calculate a current analyte concentration value using at least the analyte data and the acceleration data.

14. The method of claim 13, further comprising using the display device to generate activity information based on the acceleration data, wherein calculating the current analyte concentration value using at least the analyte data and the acceleration data comprises calculating the current analyte concentration value using at least the analyte data and the activity information generated based on the acceleration data.

15. The method of claim 13, wherein the wearable transceiver comprises the accelerometer.

16. A method comprising:

using an analyte sensor to generate analyte data;

using an accelerometer to generate acceleration data corresponding to movement of the accelerometer;

using a controller of a wearable transceiver to store the analyte data with the acceleration data and date and time information in a memory of the wearable transceiver;

using the controller of the wearable transceiver to cause a display device interface of the wearable transceiver to convey the analyte data, the acceleration data, and the date and time information to a display device;

using the display device to receive the analyte data, the acceleration data, and the date and time information conveyed by the wearable transceiver; and using the display device to generate activity information based on the acceleration data, wherein generating the activity information based on the acceleration information comprises:

converting the acceleration data into scalar acceleration values;

comparing the scalar acceleration values to an activity threshold; and generating the activity information based on a frequency at which the scalar acceleration values exceed the activity threshold.

17. The method of claim 16, further comprising using the display device to calculate an analyte concentration value using at least the analyte data.

18. The method of claim 17, wherein the display device calculates the analyte concentration value using at least the analyte data and the activity information.

19. The method of claim 17, further comprising using the display device to display the analyte concentration value together with the activity information.

20. The method of claim 17, further comprising using the display device to display a plot of analyte concentration values and activity information with respect to time.

21. The method of claim 17, further comprising using the display device to generate an alert for a current or projected physiological condition or reaction based on the analyte concentration value and the activity information.

* * * * *